United States Patent [19]

Weir

[11] 3,998,821

[45] Dec. 21, 1976

[54] PROCESS FOR PREPARING CEPHALOSPORIN COMPOUNDS

[75] Inventor: Niall Galbraith Weir, London, England

[73] Assignee: Glaxo Laboratories Limited, Greenford, England

[22] Filed: Aug. 9, 1974

[21] Appl. No.: 496,330

Related U.S. Application Data

[62] Division of Ser. No. 167,870, July 30, 1971, Pat. No. 3,853,860.

[30] Foreign Application Priority Data

Aug. 6, 1970 United Kingdom ............ 38020/70
July 15, 1971 United Kingdom ............ 38020/70

[52] U.S. Cl. .......................... 260/243 C; 424/246
[51] Int. Cl.$^2$ ...................... C07D 501/02

[58] Field of Search ................ 260/243 C

[56] References Cited

UNITED STATES PATENTS

| 3,823,139 | 7/1974 | Elphinstone et al. | 260/243 C |
| 3,823,140 | 7/1974 | Clark et al. | 260/243 C |
| 3,853,860 | 12/1974 | Weir | 260/243 C |

Primary Examiner—Nicholas S. Rizzo
Attorney, Agent, or Firm—Bacon & Thomas

[57] ABSTRACT

The invention is concerned with the preparation of $\Delta^3$-4-carboxy cephalosporin antibiotics possessing a 3-ethyl or substituted 3-ethyl group by means of phosphorous intermediates.

6 Claims, No Drawings

PROCESS FOR PREPARING CEPHALOSPORIN COMPOUNDS

This application is a division of application Ser. No. 167,870 filed July 30, 1971 now U.S. Pat. No. 3,853,860 issued Dec. 10, 1974.

This invention is concerned with improvements in or relating to cephalosporin compounds.

The cephalosporin compounds referred to in this specification are generally named with reference to cepham (see J. Amer. Chem. Soc. 1962, 84, 3400). The term "cephem" refers to the basic cepham structure with one double bond. Where a dotted line bridges the 2-, 3- and 4-positions this indicates that the compound may be a ceph-2-em or a ceph-3-em compound.

My invention is concerned with a novel group of cephalosporin compounds that are of value as intermediates in the production of cephalosporin compounds possessing antibacterial activity. As is well known in the art $\Delta^3$-4-carboxy cephalosporin antibiotics are compounds which are generally depicted by the formula

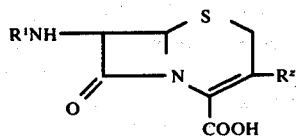

(wherein $R^1$ is a carboxylic acyl group and $R^z$ is the 3-position substituent). My new intermediates are of value in that they can be used to produce a variety of cephalosporin antibiotics characterized by possessing an ethyl or substituted ethyl group as 3-position substituent.

My new cephalosporin compounds possess a phosphoranylidene ethyl group at the 3-position and may be prepared by reacting a corresponding 3-halomethyl compound with a particular class of carbanions derived from phosphorus ylids.

The phosphoranylidene ethyl group may be depicted as follows

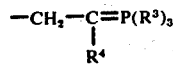

wherein $R^4$ is an organic group or a hydrogen atom and the $R^3$ groups, which may be the same or different, are each organic groups. In subsequent transformations the moiety $P(R^3)_3$ will generally be displaced so that the nature of the group $R^3$ is not critical.

Compounds containing the phosphoranylidene group may be reacted with an acid HX to form compounds possessing the group

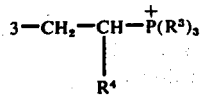

wherein $R^3$ and $R^4$ have the above defined meanings and $X^-$ is the anion of the acid HX. It will be understood that such acid addition salts fall within the scope of the invention. Acids which may be used to form the acid addition salts include hydrochloric, hydrobromic and hydroiodic acid.

The group $R^3$ may, for example, be $C_3$–$C_{10}$ alkyl, $C_5$- or $C_6$- cycloalkyl, aryl e.g. phenyl or substituted phenyl, di(lower alkyl) amino, etc.

Compounds according to the invention may thus have the formula

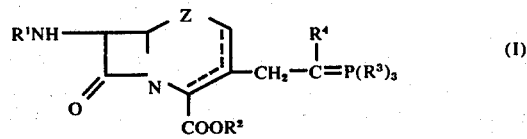

(wherein $R^1$ is a carboxylic acyl group, $R^2$ is hydrogen or a carboxyl-blocking group, Z is >S or >S → O and $R^3$ and $R^4$ have the above defined meanings).

The group $R^1$ in the above formula may represent a wide variety of acyl groups which may contain 1–20 carbon atoms. Specific acyl groups are illustrated in the accompanying list which is not intended to be exhaustive:

i. $R^u C_n H_{2n} CO$— where $R^u$ is aryl (carbocyclic or heterocyclic), cycloalkyl, substituted aryl, substituted cycloalkyl, cyclohexadienyl, or a non-aromatic heterocyclic or mesoionic group, and $n$ is an integer from 1–4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis (2-chloroethyl) aminophenylpropionyl; thien-2- and 3-ylacetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl isoxazol-4-yl group, the aryl group being e.g. phenyl or halophenyl e.g. chloro- or bromo- phenyl. An acyl group of this type is 3-o-chlorophenyl-5-methylisoxazol-4-ylacetyl.

ii. $C_n H_{2n+1} CO$— where $n$ is an integer from 1–7. The alkyl group may be straight or branched and, if desired, may be interrupted by an oxygen or sulphur atom or substituted by e.g. a cyano group, a carboxy group, an alkoxycarbonyl group, a hydroxy group or a carboxycarbonyl group (—CO.COOH). Examples of such groups include cyanoacetyl, hexanoyl, heptanoyl, octanoyl and butylthioacetyl.

iii. $C_n H_{2n-1} CO$— where $n$ is an integer from 2–7. The alkenyl group may be straight or branched and, if desired, may be interrupted by an oxygen or a sulphur atom. An example of such a group is allylthioacetyl.

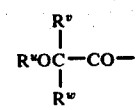

where $R^u$ has the meaning defined under (i) and in addition may be benzyl, an $R^v$ and $R^w$ which may be the same or different each represent hydrogen, phenyl, benzyl, phenethyl or lower alkyl. Examples of such groups include phenoxyacetyl, 2-phenoxy-2-phenylacetyl, benzyloxyacetyl, 2-phenoxypropionyl, 2-phenoxybutyryl, methylthiophenoxyacetyl.

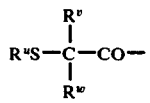

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

vi. $R^u Z(CH_2)_m CO-$ where $R^u$ has the meaning defined under (i) and, in addition, may be benzyl, Z is an oxygen or sulphur atom and $m$ is an integer from 2–5. An example of such a group is S-benzylthiopropionyl.

vii. $R^u CO-$ where $R^u$ has the meaning defined under (i). Examples of such groups include benzoyl, substituted benzoyl (e.g. aminobenzoyl), 4-isoxazolyl- and substituted 4-isoxazolylcarbonyl, cyclopentanecarbonyl, sydnonecarbonyl, naphthoyl and substituted naphthoyl (e.g. 2-ethoxynaphthoyl), quinoxalinylcarbonyl and substituted quinoxalinylcarbonyl (e.g. 3-carboxy-2-quinoxalinylcarbonyl). Other possible substituents for benzoyl include alkyl, alkoxy, phenyl, phenyl substituted by carboxy, alkylamido, cycloalkylamido, allylamido, phenyl(lower)alkylamido, morpholinocarbonyl, pyrrolidinocarbonyl, piperidinocarbonyl, tetrahydropyridino, furfurylamido or N-alkyl-N-anilino, or derivatives thereof, and such substituents may be in the 2- or 2- and 6- positions. Examples of such substituted benzoyl groups are 2,6-dimethoxybenzoyl, 2-methylamidobenzoyl and 2-carboxybenzoyl. Where the group $R^u$ represents a substituted 4-isoxazolyl group, the substituents may be as set out above under (i). Examples of such 4-isoxazolyl groups are 3-phenyl-5-methyl-isoxazol-4-yl carbonyl, 3-o-chlorophenyl-5-methyl-isoxazol-4-yl carbonyl and 3-(2,6-dichlorophenyl)-5-methyl-isoxazol-4-yl carbonyl.

viii.

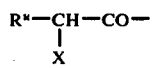

where $R^u$ has the meaning defined under (i) and X is amino, substituted amino (e.g. acylamido or a group obtained by reacting the α-aminoacylamido group of the 7-side chain with an aldehyde or ketone e.g. acetone, methylethylketone or ethyl acetoacetate), hydroxy, carboxy, esterified carboxy, azido, triazolyl, tetrazolyl, cyano, halogeno, acyloxy (e.g. formyloxy or lower alkanoyloxy) or etherified hydroxy group. Examples of such acyl groups are α-aminophenylacetyl, and α-carboxyphenylacetyl.

ix.

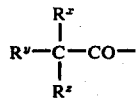

where $R^x$, $R^y$ and $R^z$ which may be the same or different may each represent lower alkyl, phenyl or substituted phenyl or $R^x$ represents hydrogen. An example of such an acyl group is triphenylmethylcarbonyl.

x. $R^u-NH-CO-$ where $R^u$ has the meaning defined under (i) and in addition may be hydrogen, lower alkyl or halogen substituted lower alkyl. An example of such a group is $Cl(CH_2)_2 NHCO$.

xi.

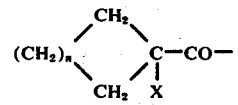

where X has the meaning defined under (viii) above and $n$ is an integer of from 1 to 4. An example of such an acyl group is 1-aminocyclohexanecarbonyl.

xii. Amino acyl, for example $R^w CH(NH_2).(CH_2)_n CO-$ where $n$ is an integer from 1–10, or $NH_2.C_n H_{2n} Ar(CH_2)_m CO$, where $m$ is zero or an integer from 1–10, and $n$ is 0, 1 or 2, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British Patent Specification No. 1,054,806. A group of this type is the p-aminophenylacetyl group. Other acyl groups of this type include those, e.g. 5-aminoadipoyl, derived from naturally occurring amino acids, and derivatives thereof e.g. N-benzoyl-5-aminoadipoyl.

xiii. Substituted glyoxylyl groups of the formula $R^y.CO.CO-$ where $R^y$ is an aliphatic, araliphatic or aromatic group, e.g. a thienyl group, a phenyl group, or a mono-, di- or tri- substituted phenyl group, the substituents being, for example, one or more halogen atoms (F, Cl, Br, or I), methoxy groups, methyl groups or amino groups, or a fused benzene ring. Included in this group are also the α-carbonyl derivatives of the above substituted glyoxylyl groups.

xiv. Formyl.

If it is intended to effect a subsequent reaction on the compound of formula I two important species of $R^1$ groups are:

xv. Hydrocarbyloxycarbonyl and substituted hydrocarbyloxycarbonyl groups (wherein the 7-amino group forms part of a urethane), e.g. lower alkoxycarbonyl groups (such as methoxycarbonyl, ethoxycarbonyl and t-butoxycarbonyl groups); halo lower alkoxycarbonyl groups e.g. 2,2,2-trichloroethoxycarbonyl; aralkoxycarbonyl groups such as benzyloxycarbonyl, 4-methoxybenzyloxycarbonyl, diphenylmethoxycarbonyl and 4-nitrobenzyloxycarbonyl groups; and cycloalkoxycarbonyl groups e.g. adamantyloxycarbonyl.

xvi. Haloformyl e.g. chloroformyl.

The invention also comprises a process for the preparation of the compounds of formula I which comprises reacting a 3-halo-(i.e. bromo-, iodo- or chloro) methyl cephalosporin compound with a phosphorus yield of formula III below. This aspect of the invention will now be described in greater detail with reference to the cephalosporin starting materials, the phosphusylid, the reaction conditions and subsequent transformations.

CEPHALOSPORIN STARTING MATERIALS

The 3-halomethyl cephalosporin compounds used as starting materials may be defined as having the general formula

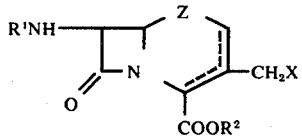

II wherein $R^1$, $R^2$ and Z have the above-defined meanings and X is bromine, iodine or chlorine.

Compounds of formula (II) where X represents Cl or Br, can be prepared from the corresponding 3—CH$_2$OH compounds by methods for the replacement of -OH by Cl or Br. For example, the 3—CH$_2$Cl compounds can be prepared from the corresponding 3—CH$_2$OH compounds by reaction with thionyl chloride, PCl$_3$, PCl$_5$, phosphorus oxychloride, phosgene, or substituted phosgenes. The 3—CH$_2$Br compounds can be similarly prepared by reaction of the corresponding bromo-compounds with the 3—CH$_2$OH compounds. The 3—CH$_2$I compounds can be prepared from the corresponding chlorides and bromides e.g. by reaction with an alkali metal iodide.

Ceph-3-em compounds of formula (II) can also be prepared by halogenation of a 3-methyl cephalosporin sulphoxide as described in Belgian Patent No. 755,256.

Ceph-2-em compounds of formula (II) may also be prepared by the method of Dutch published Patent Application No. 6902013 by reaction of a ceph-2-em-3-methyl compound with N-bromosuccinimide to yield the ceph-2-em-3-bromomethyl compound.

Compounds containing a sulphur atom at the 1-position of the cephem nucleus may be oxidised to the corresponding sulphoxides by methods analogous to those described by Chow, Hall and Hoover (J. Org. Chem. 1962, 27, 1381). The cephalosporin compound is mixed with the oxidising agent in an amount such that at least one atom of active oxygen is present per atom of thiazolidine sulphur. Suitable oxidising agents include metaperiodic acid, peracetic acid, permonophthalic acid, iodobenzene dichloride, m-chloroperbenzoic acid or t-butyl hypochlorite, the latter being preferably used in admixture with a weak base e.g. pyridine. The 1-oxide may be obtained in the α-and/or β-form.

The group protecting the 4-carboxyl group may be formed with an alcohol (aliphatic or araliphatic), phenol, silanol, stannanol or acid which may readily be split off at a later stage of the reaction.

Suitable esters thus include compounds containing as 4-ester group, a group selected from the following list which is not intended to be an exhaustive list of possible ester groups i. —COOCR$^a$R$^b$R$^c$ wherein at least one of R$^a$, R$^b$ and R$^c$ is an electron-donor e.g. p-methoxyphenyl, 2,4,6-trimethylphenyl, 9-anthryl, methoxy, acetoxy or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxycarbonyl.

ii. —COOCR$^a$R$^b$R$^c$ wherein at least one of R$^a$, R$^b$ R$^c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining R$^a$, R$^b$ and R$^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. —COOCR$^a$R$^b$R$^c$ wherein at least two of R$^a$, R$^b$ and R$^c$ are hydrocarbon such as alkyl e.g. methyl or ethyl, or aryl e.g. phenyl and the remaining R$^a$, R$^b$ and R$^c$ group, if there is one, is hydrogen. Suitable esters of this type include, t-butyloxycarbonyl, t-amyloxycarbonyl, diphenylmethoxycarbonyl and triphenylmethoxycarbonyl.

iv. —COOR$^d$ wherein R$^d$ is adamantyl, 2-benzyloxyphenyl, 4-methylthiophenyl, tetrahydropyran-2-yl or tetrahydrofur-2-yl.

Silyl esters may conveniently be prepared from a halosilane or a silazane of the formula R$^4{}_3$SiX; R$^4{}_2$SiX$_2$; R$^4{}_3$Si.NR$^4{}_2$; R$^4{}_3$Si.NH.SiR$^4{}_3$; R$^4{}_3$Si.NH.COR$^4$; R$^4{}_3$Si.NH.CO.NH.SiR$^4{}_3$; R$^4$NH.CO.NR$^4$.SiR$^4{}_3$; or R$^4$C(OSiR$^4{}_3$):NSiR$^4{}_3$ where X is a halogen and the various groups R$^4$, which can be the same or different, represent hydrogen atoms or alkyl, e.g. methyl, ethyl, n-propyl, iso-propyl; aryl, e.g. phenyl; or aralkyl e.g. benzyl groups.

Preferred derivatives of silanols are silyl chlorides such as for example trimethylchlorosilane and dimethyldichlorosilane.

The carboxyl groups may be regenerated from an ester by any of the usual methods; for example, acid- and base-catalysed hydrolysis (especially for silyl and stannyl esters) is generally applicable, as well as enzymically-catalysed hydrolyses; however, aqueous mixtures may be poor solvents for these compounds and they may cause isomerizations, rearrangements, side-reactions, and general destruction, so that special methods may be desirable. Five suitable methods of deesterification are:

i. Reactions with Lewis acids: Suitable Lewis acids for reaction with the esters include trifluoracetic acid, formic acid, hydrochloric acid in acetic acid, zinc bromide in benzene and aqueous solutions or suspensions of mercuric compounds. The reaction with the Lewis acid may be improved by addition of a nucleophile such as anisole.

ii. Reduction: Suitable systems for effecting reduction are zinc/acetic acid, zinc/formic acid, zinc/lower alcohol, zinc/pyridine. palladised-charcoal and hydrogen, electrolysis, and sodium and liquid ammonia.

iii. Attack by nucleophiles: Suitable nucleophiles are those containing a nucleophilic oxygen or sulphur atom for example alcohols, mercaptans, thiocyanates and water.

iv. Oxidative methods: for example, those which involve the use of hydrogen peroxide and acetic acid.

v. Irradiation.

PHOSPHORUS YLID.

Phosphorus ylids which may be used in the process according to the invention include those having the general formula

(III)

wherein $R^3$ and $R^4$ have the above defined meanings.

When employing ceph-3-em compounds as the sulphides we prefer that the phosphorus ylid is chosen from those having a pKa (in water: ethanol = 8:2 v/v) of from 6.5 to 12 at 25° to facilitate the desired reaction.

The nature of $R^4$ will depend on the nature of the compound to be produced and the reaction conditions involved. When employing ceph-3-em compounds $R^4$ should be an electronegative group. Suitable electronegative groups include ester groups, acyl groups, nitro groups and nitrile groups. Thus the electronegative group may be $-CO_2R^5$, $-COR^6$, $-CON(R^6)_2$, $-S(O)R^5$, $-S(O)_2R^5$, $-NO_2$ or $-CN$ wherein $R^5$ may represent an alkyl group, e.g. a lower alkyl group such as methyl, ethyl, n-propyl or isopropyl; an aralkyl group such as benzyl; an aryl group such as phenyl or naphthyl; or a cycloalkyl group such as cyclohexyl or cyclopentyl, and $R^6$ is a hydrogen atom or any of the $R^5$ groups.

When employing ceph-2-em compounds, the nature of $R^4$ is not so critical; it may or may not be electronegative and may be selected from hydrogen, lower alkyl, cycloalkyl, aromatic e.g. phenyl, etc. groups.

If desired, the ylid (III) may be generated without purification by reaction with a base stronger than the conjugate base of the phosphonim compound. Suitable bases include alkaline earth metal hydroxides, carbonates and hydrogen carbonates e.g. sodium hydrogen carbonate. Other bases which may be used to generate ylids include nitrogen bases such as trialkylamines, carbanions, for example as provided by the conjugate base of dimethylacetamide, and other ylids; the sodio or lithio derivatives of hexamethyldisilazane, alkali metal hydrides, alkylene oxides (e.g. ethylene oxide or propylene oxide) which may be generated with halide ion, and fluoride ion in an aprotic solvent.

The reactant ylid (III) must be used in an amount of at least one molar proportion either in association with a base stronger than the conjugate base of the phosphonium compound or in association with a further molar proportion of the ylid (III) which itself may function as the desired base.

The use of a base at this stage in conjunction with a ceph-2-em compound may convert the cephalosporin compound to a ceph-3-em compound. This enables a convenient isomerisation to be simultaneously effected.

REACTION CONDITIONS

The reaction may be carried out by stirring the components together, e.g. at a temperature of from $-80°$ to $+80°$ C, preferably from $-10°$ to $+35°$ C. When the reaction is effected at a temperature at which one or more reactants may volatilise a closed system may be used. The reaction may be effected in an inert or relatively inert solvent, for example, a halogenated hydrocarbon, e.g. methylene chloride; a hydrocarbon e.g. benzene; an acyclic or cyclic ether e.g. diethyl ether, tetrahydrofuran or dioxan; dimethylsulphoxide; an amide e.g. dimethylformamide or dimethylacetamide; an ester e.g. a lower alkyl alkanaoate such as ethyl acetate, or hexamethylphosphoramide. The course of the reaction may also be followed by thin-layer or paper chromatography, by electrophoresis and by spectroscopy.

Although we do not wish to be bound by theoretical considerations it is believed that the reaction of the 3-halomethyl cephalosporin compound of formula (II) with the phosphorus ylid of formula (III) to form a compound of formula (I) proceeds as follows:

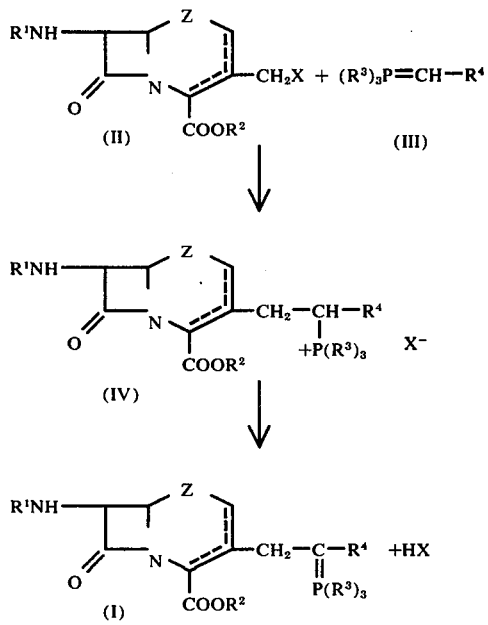

SUBSEQUENT TRANSFORMATIONS

The compounds of the invention may be used to produce a variety of cephalosporin antibiotics.

Thus, compounds of the general formula

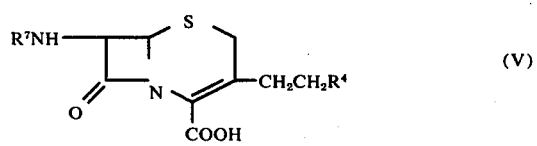

(wherein $R^7$ is a carboxylic acyl group which may be the group $R^1$, and $R^1$ and $R^4$ have the above-defined meanings) and non-toxic derivatives thereof may be prepared from a compound of formula (I) by (A) cleavage of the carbon-phosphorus bond. Any of the following reactions (B) may be carried out before or after said cleavage (i) conversion of a $\Delta^2$-isomer into the desired $\Delta^3$-isomer (ii) removal of any groups protecting any carboxyl groups (iii) reduction of a compound in which Z is $>S \rightarrow O$ to form the desired $Z =>S$ compound and (iv) deacylation of a compound in which $R^7$ does not equal $R^1$ to form a 7-amino compound followed by reacylation to introduce the desired $7-R^7NH-$ group.

Cleavage of the carbon-phosphorus bond may be achieved by, for example, reduction or by hydrolysis. Reduction may be effected with the aid of aluminium amalgam, palladised charcoal/hydrogen or zinc/HCl.

Compounds of formula (V) wherein $R^4$ is an alkoxycarbonyl group are novel compounds useful as cephalosporin antibiotics. The invention thus includes within its scope compounds of the general formula

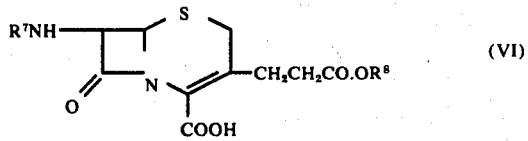

(VI)

wherein $R^7$ has the above-defined meaning and $R^8$ is lower alkyl.

Compounds of general formula (VI) and non-toxic derivatives thereof, e.g. base salts (where applicable) and acid addition salts (where applicable), possess antibacterial activity against a range of organisms and are of value in human and veterinary medicine. They may also be of value in the preparation of other 3-substituted cephalosporin compounds. By the term "non-toxic" as applied to the fompounds of formula (VI) we mean those derivatives which are physiologically acceptable in the dosage at which they are administered.

Salts which may be formed from the compounds according to the invention include (a) inorganic base salts such as alkali metal e.g. sodium and potassium, alkaline earth e.g. calcium, and organic base salts e.g. procaine and dibenzylethylene diamine salts and (b) acid addition salts of any possible basic functions e.g. amino e.g. with hydrochloric hydrobromic, sulphuric, nitric, phosphoric, toluene-p-sulphonic and methanesulphonic acids. The salts may also be in the form of resinates, formed, e.g. with a polystyrene resin containing amino, quaternary amino, or sulphonic acid groups, or a resin containing carboxyl groups, e.g a polyacylic acid resin. The resin may if desired be cross-linked, e.g. it may be a copolymer of styrene and divinylbenzene containing the appropriate groups.

There will now be discussed subsequent reactions (B) that may be effected before, but preferably after, the cleavage reaction discussed above.

Where the resultant compound contains a sulphinyl group at the 1-position this may be reduced by any convenient means. This may, for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Alternatively, reduction of the 1-sulphinyl group may be effected by phosphorus trichloride or tribromide in solvents such as methylene chloride, dimethylformamide or tetrahydrofuran, preferably at a temperature of −20° C to +50° C.

An advantage associated wih the use of a sulphoxide is that the compound will generally be a $\Delta^3$-compound.

Where the resultant compound is a ceph-2-em compound, th desired ceph-3-em compound may be obtained by treatment of the former with a base.

Removal of any groups protecting any amino or carboxyl groups may be effected as described above.

Where the final product of the above reactions is a 7β-acylamido compound not having the desired acyl group, the 7β-acylamido compound may be N-deacylated to yield the corresponding 7β-amino compound and the latter acylated with an appropriate acylating reagent.

Suitable methods of N-deacylating cephalosporin derivatives having 7β-acylamido groups are described in British Patents Nos. 1,041,985 and 1,119,806; Belgian Patent No. 719,712 and in South African Patent Specification Nos. 68/5048 and 68/5327. Another method of N-deacylation which may be used is acid catalysis. For example, N-deformylation of a 7β-formamido group may be effected wih a mineral acid at a temperature of minus 15° to 100° C, preferably +15° to 40° C. N-deformylation may be effected with the acid of a Lewis acid in a lower alkanol, preferably under substantially anhydrous conditions.

The compounds of formula (VI) may be formulated for administration in any convenient way, by analogy with other antibiotics and the invention therefore includes within its scope a pharamaceutical composition comprising a compound of formula (VI) or a non-toxic derivative e.g. salf thereof (as herein defined) adapted for use in human or veterinary medicine. Such compositions may be presented for use in conventional manner with the acid of any necessary pharamaceutical carriers or excipients. The compoditions may contain from 0.1% upwards, preferably from 10–16% of the active material, depending on the method of administration. Where the compositions comprise dosage units, each unit will preferably contain 50–500 mg. of the active ingredient. The dosage as employed for adult human treatment will preferably range from 100–3000 mg. for instance 1500 mg. per day, depending on the route and frequency of administration.

Compounds of formula (VI) according to the invention may be administered in combination with other therapeutic agents such as antibiotics, for example other cehalosporins, the penicillins or tetracyclines.

The following examples illustrate the invention. In the Examples:

System B is n-butanol:ethanol-water = 4:1:5, equilibrated at room temperature, the upper phase being used as developer in descending manner, in equilibrium with lower phase, on Whatman No. 1 paper buffered to pH 6 with 0.05M sodium dihydrogen phosphate.

System C is ethyl acetate: n-butanol: 0.1M-sodium acetate pH 5 = 8:1:8, equilibrated at 38°C, the upper phase being used as developer in descending manner, in equilibrium with lower phase at 38°, on No. 1 Whatman paper buffered to pH 5 with 0.1M sodium acetate.

Light petroleum was the fraction, b.p. 40° to 60°. Methylene chloride was dried on Woelm Grade I basic alumina. Thin-layer chromatography was carried out upwards on Merck silica plates.

Nmr spectra were measured at 60 and 100 Mhz. Signs of the coupling constants cannot be attributed.

As far as possible, analytical values for solvates were confirmed by inspection for the appropriate features in the spectra.

The conditions for electrophoresis are those described by Cocker et al., *J. Chem. Soc.*1965, 5015.

Organic solutions were dried over desiccated magnesium sulphate.

EXAMPLE 1

3-(2-Ethoxycarbonylethyl)-7β-(2-thienylacetamido) ceph-3-em-4-carboxylic Acid

The title compound was prepared via the following reaction scheme. The steps are described in more detail below.

t-Butyl 3-hydroxymethyl-7β-(2-thienylacetamido)-ceph-3-em-4-carboxylate

↓a.

t-Butyl 3-chloromethyl-7β-(2-thienylacetamido)ceph-3-em-4-carboxylate

↓b.

t-Butyl 3-iodomethyl-7β-(2-thienylacetamido)ceph-3-em-4-carboxylate

↓c.

t-Butyl 3-(2-ethoxycarbonyl-2-triphenylphosphoranylideneethyl)-7β-(2-thienylacetamido)ceph-3-em-4-carboxylate ↓d.

t-Butyl 3-(2-ethoxycarbonylethyl)-7β-(2-thienylacetamido) ceph-3-em-4-carboxylate ↓e.

3-(2-Ethoxycarbonylethyl)-7β-(2-thienylacetamido)-ceph-3-em-4-carboxylic acid t-Butyl 3-Chloromethyl-7β-(in -thienylacetamido)ceph-3-em-4-carboxylate

A solution of t-butyl 3-hydroxymethyl-7β-2-thienylacetamido)ceph-3-em-4-carboxylate (24 g. prepared as described in Example 6 of Belgian Patent No. 755,505) in dry peroxide-free tetrahydrofuran (180 ml.) with pyridine (18 ml., 4 equiv.) was run into a vigorously stirred mixture of thionyl chloride (8.4 ml., 2 equiv.) in tetrahydrofuran (110 ml.) at ca −25° over 40 minutes. The mixture was stirred for a further 30 minutes then poured into N-hydrochloric acid (1000 ml.) and the total extracted with ethyl acetate. The extracts were washed with water and aqueous sodium bicarbonate, then with further amounts of water, and dried and evaporated in vacuo. The residue was washed with ether to give the chloromethyl compound (18.4 g.) as a crystalline solid. This material was recrystallised from acetone (containing some ether) — petroleum to give the pure chloromethyl compound (17 g.) as prisms, m.p. with darkening 135°, [α]$_D$ −4.2° (c 1.9, CHCl$_3$), λ$_{max}$. (EtOH) 266 nm. (ε, 7,900), ν$_{max}$. (CHBr$_3$) 3460 (NH), 1790 (β-lactam), 1722 (CO$_2$R) and 1690 and 1514 cm$^{-1}$ (CONH), τ(CDCl$_3$) 3.32 (NH, doublet, J 9 Hz), 4.20 (C$_{(7)}$-H, double doublet, J 9 and 4.5 Hz), 5.07 (C$_{(6)}$-H, doublet, J 4.5 Hz), 5.47 and 5.61 (CH$_2$Cl, AB-quartet, J 12 Hz), 6.20 (CH$_2$CONH), 6.36 and 6.62 (C$_{(2)}$-CH$_2$, AB-quartet, J 18 Hz), and 8.50 (C[CH$_3$]3).

(Found : C, 50.2; H, 4.85; Cl, 7.8; N, 6.3; S, 14.8. C$_{18}$H$_{21}$ClN$_2$O$_4$S$_2$ requires C, 50.4; H, 4.9; Cl 8.3; N, 6.5; S, 14.95%).

b. t-Butyl 3-iodomethyl-7β-(2-thienylacetamido)ceph-3-em-4-carboxylate

A solution of t-butyl 3chloromethyl-7β-(2-thienylacetamido)ceph-3-em-4-carboxylate (8.58 g) in acetone (50 ml.) was treated with a solution of sodium iodide (9 g.) in acetone (50 ml.) and the mixture stirred in the dark at 20° for 2½ hours. The mixture was poured into saturated brine and extracted with ethyl acetate. The extract was washed quickly with 10% aqueous sodium thiosulphate and water, dried and evaporated in vacuo. The residue was washed with ether to give the iodomethyl compound (6.86 g.) as pale yellow prisms, m.p. 123°–127° (decomp.), [α]$_D^{23}$ −60° (c, 1.0 CHCl$_3$), λ$_{max}$. (EtOH) 228 nm. (ε 7,750),ν$_{max}$. (CHBr$_3$) 3478 (NH), 1791 (β-lactam), 1722 (CO$_2$R) and 1690 and 1516 (CONH), τ (CDCl$_3$) 3.04 (NH, doublet J 9 Hz), 4.27 (C$_{(7)}$-H, double doublet, J 9 and 4.5 Hz), 5.07 (C$_{(6)}$-H, doublet, J 4.5 Hz) 5.66 (CH$_2$I, singlet), 6.17 CH$_2$CONH), 6.6 and 6.27 (C$_{(2)}$-CH$_2$, AB-quartet, J 18 Hz), and 8.46 (C[CH$_3$]$_3$).
(Found: C, 42.2; H, 4.2 N, 5.5; S, 12.6. C$_{18}$H$_{21}$IN$_2$O$_4$S$_2$ requires: C, 41.5; H, 4.05; N, 5.4; S, 12.3%).

c. t-Butyl 3-(2-Ethoxycarbonyl-2-triphenylphosphoranylideneethyl)-7β-(2-thienylacetamido)-3-em-4-carboxylate A solution of t-butyl 3-iodomethyl-7β-(2-thienylacetamido)ceph-3-em-4-carboxylate (3.65 g., 7 mmole) in ethyl acetate (40 ml.) was treated with a solution of ethoxycarbonylmethylenetriphenylphosphorane (4.9 g., 14 mmole) in ethyl acetate (50 ml) and the mixture stirred at 3° for 18 hours. Material which had crystallised out after this period was isolated by filtration and dissolved in methylene dichloride (ca 50 ml.). The organic solution was washed with N-hydrochloric acid (3 × ca 50 ml.), water (3 × ca 50 ml.), half saturated aqueous sodium bicarbonate solution (2 × ca 50 ml.) and finally water (2 × ca 50 ml.), and dried and evaporated in vacuo. The residual foam was crystallised from ethyl acetate to give the title compound (3.35 g., 64.5%) as photosensitive prisms m.p. (darkening at 168°) 174° (decomp.). [α]$_D^{22}$ +60° (c 1.5, CHCl$_3$), λ$_{max}$. (EtOH) 226 nm. (ε, 9,920) and 272 nm. (ε, 9,470) ν$_{max}$. (CHBr$_3$) 3390 (NH), 1780 (β-lactam), 1710 (CO$_2$R), 1680 and 1518 (CONH), and 1605 cm$^{-1}$ (P=CCO$_2$Et), p.m.r. spectrum showed ca ½ mole ethyl acetate which masked some of the CO$_2$Et bands. A sample (280 mg.) was recrystallised from acetone to give the phosphorane (200 mg.) as photosensitive white prisms, m.p. (darkening at 168°) 176° decomp. [α]$_D$+64.3° (c 1.4 CHCl$_3$), λ$_{max}$. (EtOH) 226 nm. (ε, 10,200) and 272.2 nm (ε, 9,700), ν$_{max}$. (nujol) 3230 and 3195 (NH), 1775 (β-lactam), 1712 (—CO$_2$R), 1582 and 1590 (p=CCO$_2$Et; corresponding to two rotational isomers), 1675 and 1542 (CONH) and 1438 cm$^{-1}$ (P Ph$_3$), ν$_{max}$. (CHBr$_3$) 3390 (NH), 1780 (β-lactam), 1710 (CO$_2$R), 1680 and 1518 (CONH), 1605 (P=CCO$_2$Et) and 1445 cm$^{-1}$ (P Ph$_3$), τ (CDCl$_3$) 3.4 (NH doublet, J 9 Hz), 4.44 (C$_{(7)}$-H double doublet, J9 and 4.5 Hz), 5.3 (C$_{(6)}$-H, doublet, J 4.5 Hz), ca 6.0 (OCH$_2$CH$_3$, complex) 6.22 (CH$_2$CONH), 6.1 to 6.7 (C$_{(3)}$-CH$_2$ and CH$_2$C=P complex), 7.87 (acetone ca ⅓ mole), 8.65 (C[CH$_3$]$_3$) 8.84 and 9.55 (OCH$_2$CH$_3$, two triplets in ratio 1:2 [total 3 protons] corresponding to rotational isomers [see H.I. Zelinger, J.P. Snyder and H.J. Bestmann, Tetrahedran Letters 1969, 2199]).

(Found: C, 65.2; H, 5.65; N, 3.55; P, 4.3; S, 8.7; C$_{40}$H$_{41}$N$_2$O$_6$PS$_2$166 CH$_3$COCH$_3$ requires C, 64.8; H, 5.7; N, 3.7; P, 4.1; S, 8.45%).

d. t-Butyl 3-(2-Ethoxycarbonylethyl)-7β-(2-thienylacetamido)-ceph3-em-4-carboxylate A solution of t-butyl 3-(2-ethylcarbonyl-2-triphenylphosphoranylideneethyl)-7β-(2-thienylacetamido)-ceph-3-em-4-carboxylate (500 mg.) in tetrahydrofuran (10 ml.) was treated with aluminum amalgam (500 mg., prepared as described in L.G. Fiester and M.

Fieser, Reagents for Organic Synthesis, P. 20) and water (0.2 ml.), and the mixture stirred at 23°After 2 and 3 hours further amounts (0.2 ml., and 0.1 ml. respectively) of water were added. After a total of 4 hours the mixture was filtered and the filtrate evaporated in vacuo. The residue was dissolved in benzene and filtered through a short column of Merck Kieselgel (0.05 - 0.2mm, 10 g.) to give, on evaporation, triphenylphosphine (130 mg., 73%). Further elution with benzene ethyl acetate (1:1) gave the title compound (230 mg., 72%) as a foam, $\lambda_{max}$. (EtOH) 270 nm ($\epsilon$, 5,020), $\nu_{max}$. (CHBr$_3$) 3450 and 3360 (NH), 1786 ($\beta$-lactam), 1730 (CO$_2$R) and 1686 and 1518 cm$^{-1}$ (CONH), $\tau$(CDCl$_3$) 3.51 (NH, doublet, J 9 Hz), 4.26 (C$_{(7)}$-H, double doublet, J 9 and 4.5 Hz), 5.09 (C$_{(6)}$-H, doublet, J 4.5 Hz), 5.88 and 8.74 (OCH$_2$CH$_3$, quartet and triplet), 6.17 (CH$_2$CONH), 6.50 and 6.8 (C$_{(2)}$-CH$_2$, AB-quartet, J 18 Hz), 7.3–7.7 (—CH$_2$CH$_2$—0—, 4 proton multiplet) and 8.47 (C[CH$_3$]$_3$).

e.
3-(2-Ethoxycarbonylethyl)-7$\beta$-(2-thienylacetamido)-ceph-3-em-4-carboxylic Acid t-Butyl 3-(2-ethoxycarbonylethyl)-7$\beta$-(2-thienylacetamido)ceph-3-em-4-carboxylate (500 mg.) with anisole (0.5 ml) was treated with trifluroacetic acid (2 ml.). After ca 5 minutes at 23° the solvents were removed in vacuo. The residue was partitioned between ethyl acetate and dilute aqueous sodium bicarbonate solution. The alkaline solution was extracted thoroughly with further amounts of ethyl acetate, then taken to pH 2 with N-hydrochloric acid. The mixture was extracted with ethyl acetate and the extracts washed with water, then dried and evaporated in vacuo. The residue was dissolved in ethyl acetate and the solution run into vigorously stirred petroleum ether (b.p. 40° to 60°) to give the acid (215 mg.) as an amorphous solid, m.p. ca 65°, [$\alpha$]$_D$ + 73° (C 1.0, 2% NaHCO$_3$), $\lambda_{max}$ (0.1 M - pH 6 phosphate buffer) 259.5 nm. ($\epsilon$ 6,280), $\nu_{max}$ (Nujol) ca 3,500 (H$_2$O), 3320 (NH), ca 2600 and 1700 (CO$_2$H), 1780 ($\beta$-lactam), 1730 (CO$_2$R) and 1670 and 1540 cm$^{-1}$ (CONH), $\tau$(D$_2$O, with NaHCO$_3$) 2.68 and 2.96 (thienyl), 4.41 (C$_{(7)}$-H, doublet, J 4.5 Hz), 4.96 (C$_{(6)}$-H, doublet, J 4.5 Hz.), 5.84 (CO$_2$CH$_2$CH$_3$, quartet), 6.12 (CH$_2$CONH), 6.48 and 6.88 (C$_{(2)}$-CH$_2$, AB-quartet, J 18 Hz), 7.1 to 7.7 (CH$_2$CH$_2$CO, ABCD-complex), and 8.75 (CO$_2$CH$_2$CH$_3$, triplet)

(Found: C, 49.7; H, 4.9; N, 6.4; S, 14.6. C$_{18}$H$_{20}$N$_2$O$_6$S$_2$, ½H$_2$O required C, 49.9; H, 4.9; N, 6.45; S, 14.8%).

Rf. 0.7 (System B) and Rf 0.34 (System C).

EXAMPLE 2 t-Butyl 3-(2-ethoxycarbonyl-2-triphenylphosphoranylideneethyl)-7$\beta$-formamidoceph-3-em-4-carboxylate a. t-Butyl 3-bromomethyl7$\beta$-formamidoceph-3-em-4-carboxylate A solution of t-butyl 3-bromomethyl-7$\beta$-formamidoceph 3-em-4-carboxylate 1$\epsilon$-oxide 8 3.95g prepared as described in Preparation A4(a), (b) and (c) and Examples B4(i) of Belgian Pat. No. 755,256]in dry methylene dichloride (85 ml.) was cooled to −20° and phosphorus tribromide (1.43 ml.) in methylene dichloride (9 ml.) added. After 17 minutes the mixture was treated with 5% aqueous sodium bicarbonate (until alkaline) and the organic layer separated and washed with water and dried and evaporated in vacuo to give the title compound (3.45 g., 91%) as a cream-coloured foam [$\alpha$] D$_{22}$ +19.3° (c 0.9, CHCl$_3$), $\lambda_{max}$. (EtOH) 270.6 nm ($\epsilon$, 5,280). $\nu_{max}$. (CHBr$_3$) 3420 (NH), 1790 ($\beta$-lactam), 1720 (CO$_2$R) and 1700 and 1505 (H.CONH), $\tau$ (CDCl$_3$) 1.76 (CHO), 3.26 (NH, doublet, J 9 Hz), 4.17 (C$_{(7)}$-H, double doublet, J 4.5 HZ), 5.02 (C$_{(6)}$-H, doublet, J 4.5 Hz), 5.61 (CH$_2$BR, singlet), 6.29 and 6.57 (C$_{(2)}$-CH$_2$, AB-quartet, J 18 Hz) and 8.47 (C[CH$_3$]$_3$)

b. t-Butyl 3-(2-Ethoxycarbonyl-2-triphenylphosphoranylidennethyl)-7$\beta$formamidoceph-3-em-4-carboxylate A solution of t-butyl 3-bromomethyl-7$\beta$-formamidoceph-3-em-4-carboxylate (550 mg.) in ethyl acetate (10 ml.) was treated with a solution of ethoxycarbonylmethylenetriphenylphosphorane (1.04 g., 2 equiv.) in ethyl acetate (15 ml.) and the mixture stirred at 3° for 18 hours. The material which had crystallised out after this time was isolated by filtration and dissolved in methylene dichloride (ca 20 ml.). The organic solution was washed successively with 2 N-hydrochloric acid (3 × 10 ml), water (3 × 10 ml.) and saturated sodium bicarbonate solution (7.5 ml.) containing an equal volume of water, and finally with water (10 ml.), then dried, and evaporated in vacuo. The residue was crystallised from ethyl acetate to give the title phosphorane-ester (220 mg.) as prisms. The original filtrate was evaporated in and the residue, in methylene dichloride, was washed as described above. Crystallisation of the material obtained, after this treatment, from ethyl acetate gave a further crop of the phosphorane-ester (57 mg.). The combined crops (277 mg., 28%) were crystallised from acetone to give the pure title compound (170 mg.) as photosensitive white prisms, m.p. (darkening at ca 172°) 186° (vigorous decomp.), [$\alpha$]D$_{27}$ + 117.8° )c 0.9, CHCl$_3$), $\lambda_{max}$. (CHCl$_3$) 266 ($\epsilon$ 11,220), and 271 nm. ($\epsilon$ 10,900), $\nu_{max}$. (CHBr$_3$) 3460 (NH), 1775 ($\beta$-lactam), 1710 (CO$_2$R), 1700 and 1503 (CONH), 1600 (P=CCO$_2$Et), and 1442 (P-aryl) cm.$^{-1}$, $\tau$ (CDCl$_3$) 1.86 (HCO), ca. 2.6 (Ph), 3.06 (NH, doublet, J 9 Hz.), 4.38 (C$_{(7)}$-H, double doubblet, J 4.5 and 9 Hz.), 5.28 (C$_{(6)}$-H, doublet, J 4.5 Hz.), ca 6.00 (CO$_2$CH$_2$CH$_3$), 6.2 to 6.7 (C$_{(8)}$-CH$_2$ and CH$_2$C=P, complex), 8.64 (t-butyl) and 8.84 and 9.55 CO$_2$CH$_2$CH$_3$, two triplets in ratio ca 1:2 [total 3 protons] corresponding to rotational insomers)

(Found: C, 65.1; H, 5.85; N, 4.25; P, 4.45; S,. C$_{35}$H$_{37}$N$_2$ O$_6$PS requires C, 65.25; H, 5.8; N, 4.35; P, 4.8; S, 4.95%).

The compound moves to the cathode on electrophoresis at pH 1.9.

EXAMPLE 3 t-Butyl 3-(2-Ethoxycarbonyl-2-triphenylphosphoranylideneethyl)-7$\beta$-(2-thienylacetamido)ceph-3-em-4-carboxylate A solution of t-butyl 3-bromomethyl-7$\beta$-(2-thienylacetamido)ceph-3-em-4-carboxylate (5.0 g., ca. 10.56 mmole.) in ethyl acetate (90 ml.) was treated with a solution of ethoxycarbonylmethylenetriphenylphosphorane (9.18 g, 26.4 mmole) in ehtyl acetate (110 ml.) and the mixture stirred at 27° for 22 hours, in the dark. The mixture was cooled to ca 3° and stirred for 2 hours after which time precipitated material was collected by filtration and treated as described in Example 1c to give the ylid (3.85 g, 49%) as photosensitive white prisms (from ethyl acetate), m.p. (darkening at ca 155°) ca 178° (decomp.), $[\alpha]D_{27} + 61.5°$ (C 1.6, $CHCl_3$), $\lambda_{max.}$ (EtOH) 266 nm. ($\epsilon$ 10,360) and 272 nm. ($\epsilon$ 10,000); the infrared and p.m.r. spectra resembled those of material described above in Example 1c.

EXAMPLE 4 t-Butyl 3-(2-Methoxycarbonyl-2-triphenylphosphoranylideneethyl)-7β-(2-thienylacetamido)ceph-3-em-4-carboxylate.

A solution of t-butyl 3-iodomethyl7β-(2-thienylacetamido)ceph3-em-4-carboxylate (1.04 g., ca 2 mmole.) in ethyl acetate (10 ml.) was treated with a solution of methoxycarbonylmethylenetriphenyl-phosphorane (1.4 g., ca 4.2 mmole.) in warm ethyl acetate (40 ml.) and the mixture stirred overnight at 3° in the dark. Precipitated solid (1.23 g.) was isolated by filtration and washed thoroughly with water. The insoluble material was dried in vacuo over phosphorus pentoxide, to give the title compound (584 mg., 40%) as fine needles, m.p. ca 164° (decomp.), $[\alpha]_D^{20} + 63.6°$ (c 1.5, $CHCl_3$), $\lambda$ inflex. (EtOH) 260 ($\epsilon$ 10,170) 266 $^4$($\epsilon$ 10,330) and 273 nm. ($\epsilon$ 9,880), $\nu_{max.}$ ($CHBr_3$) 3426 (NH), 1770 (β-lactam), 1710 ($CO_2R$), 1680 and 1512 (CONH), 1604 (P=C $CO_2R$) and 1440 (P-aryl) cm.$^{-1}$, $\tau$ ($CDCl_3$) 2.5 (PH), 2.77 and 3.03 (thienyl), 3.44 (NH, doublet, J 9 Hz.), 4.4 ($C_{(7)}$-H, double doublet J 4.5 and 9 Hz.), 5.25 ($C_{(6)}$-H, ill-resolved doublet), 6.21 ($CH_2CO$), ca 6.44 ($CO_2CH_3$), ca 6.61 ($\underline{CH}_2C=P$), ca 6.86 ($C_{(3)}$-$\underline{CH}_2$), and 8.64 (t-butyl)

(Found: C, 63.9; H, 5.4; N, 3.6; P, 4.0; S, 8.7. $C_{39}H_{39}N_2O_6PS_2$ requires C, 64.45; H, 5.4; N, 3.855; P. 4.25; S, 8.85%).

The initial ethyl acetate filtrate was evaporated in vacuo and the residue in methylene dichloride, washed alternatively three times with N-hydrochloric acid (25 ml), and water (25 ml.). The organic phase was then washed with aqueous sodium bicarbonate, and water, and dried and evaporated in vacuo. The residue was cyrstallised from ethyl acetate to give an additional crop of the title compound (414 mg. 28.6%) (total yield 998 mg., 68%) as needles, m.p. ca 180° (decomp.), $[\alpha]_D^{25} + 63.35°$ (c 1.6, $CHCl_3$), $\lambda$ inflex. (EtOH) 260 ($\epsilon$ 10,330), 266 ($\epsilon$ 10,330) 266 ($\epsilon$ 10,470) and ca 271.5 nm. ($\epsilon$ 10,030); the infrared and p.m.r. spectra of this material were similar to those of the first crop (Found: C, 64.7; H, 5.65; N, 3.6; P, 4.4; S, 8.85%).

EXAMPLE 5 t-Butyl 3-(2-Ethoxycarbonyl-2-triphenylphosphoranylideneethyl)-7β-(2-thienylacetamido)ceph-3-em-4-carboxylate, hydrochloride.

A solution of t-butyl 3-(2-ethoxycarbonyl-2-triphenylphosphoranylideneethyl)-7β-(2-thienylacetamido) ceph-3em-4-carboxylate (lg.) in peroxide-free dioxan (40 ml.) with water (10 ml.) was treated with concentrated hydrochloric acid (0.5 ml.) and the mixture freeze-dried to give the hydrochloride (1.06 g) as a pale-yellow amorphous solid, $[\alpha]_D^{20} + 32.2°$ (c 1.5, ; $CHCl_3$), $\lambda_{max.}$ (EtOH) 263.5 ($\epsilon$ 9,870), 268.5 ($\epsilon$ 10,650), and 275 nm. ($\epsilon$ 9,640), $\nu_{max.}$ ($CHBr_3$) 3500 ($H_2O$), 3440 (NH), 1785 (β-lactam), 1730 ($CO_2R$), 1690 and 1520 (CONH) and 1450, (P-aryl) cm$^{-1}$, $\tau$ ($CDCl_3$) (compound a mixture of diastereoisomers) 2.78 and 3.03 (thienyl), 3.42 and 3.10 (NH, two doublets), 4.22 and 4.28 ($C_{(7)}$-H, two double doublets, J 4.5 and 9 Hz.), 5.08 ($C_{(6)}$-H, doublet, J 4.5 and 9 Hz. ), 5.08 ($C_{(6)}$-H, doublet, J 4.5 Hz.), 6.03 and 9.02 ($CO_2CH_2CH_3$, quartet and triplet respectively, J 7 Hz.), 6.17 ($CH_2CO$), ca 5.6 to 7.0 ($\underline{CH}_2C=P$) and ($C_{(2)}$-$CH_2$) and 8.59 and 8.6 (t-butyl.). The compound moves to the cathode on eletrophoresis at pH 1.9.

I claim:

1. In a process for the preparation of a $\Delta^3$-4-carboxy cephalosporin having at the 3-position a group —$CH_2CH_2R^4$ wherein $R^4$ is hydrogen, —$CO_2R^5$, —$COR^6$, —$CON(R^6)_2$, —$S(O)R^5$, —$S(O)_2R^5$, nitro, lower alkyl, $C_5$ or $C_6$ cycloalkyl, phenyl or cyano; $R^5$ being lower alkyl, benzyl, phenyl, naphthyl, cyclohexyl or cyclopentyl; $R^6$ being hydrogen or $R^5$; wherein the improvement comprises the steps or reacting a $\Delta^2$- or $\Delta^3$-4-carboxy or protected carboxy cephalosporin or the 1-oxide thereof; said cephalosporin having at the 3-position a group —$CH_2$Hal in which Hal is chlorine, bromine or iodine with a phosphorus ylid of the formula

wherein the $R^3$ groups, which may be the same or different, are each $C_3$–$C_{10}$ alkyl, $C_5$ or $C_6$ cycloalkyl, phenyl or di(lower alkyl) amino and $R^4$ has the meaning defined above to provide at the 3-position a

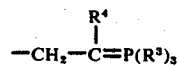

group, wherein $R^3$ and $R^4$ have the above defined meanings, and reductively cleaving the carbon to phosphorus bond to provide a cephalosporin with a —$CH_2CH_2R^4$ group at the 3-position where $R^4$ is as defined.

2. A process as claimed in claim 1 wherein reduction is effected with the aid of aluminium amalgam, palladised charcoal/hydrogen or zinc/HCl.

3. In a process for the preparation of a $\Delta^3$-4-caboxy cephalosporin having at the 3-position a group —$CH_2CH_2R^4$ wherein $R^4$ is hydrogen, —$CO_2R^5$, —$COR^6$, —$CON(R^6)_2$, —$S(O)R^5$, —$S(O)_2R^5$, nitro, lower alkyl, $C_5$or $C_6$ cycloalkyl, phenyl or cyano; $R^5$ being lower alkyl, benzyl, phenyl, naphthyl, cyclohexyl or cyclopentyl; $R^6$ being hydrogen or $R^5$; wherein the improvement comprises the steps of reacting a $\Delta^2$- or $\Delta^3$-4-carboxy or protected carboxy cephalosporin or the 1-oxide thereof; said cephalosporin having at the 3-position a group -13 $CH_2$Hal in which Hal is chlorine, bromine or iodine with a phosphorus ylid of the formula

wherein the $R^3$ groups, which may be the same or different, are each $C_3$–$C_{10}$ alkyl, $C_5$ or $C_6$ cycloalkyl, phenyl or di(lower alkyl) amino and $R^4$ has the meaning defined above to provide at the 3-position a

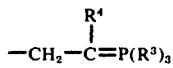

group, wherein $R^3$ and $R^4$ have the above defined meanings and cleaving the carbon to phosphorus bond by hydrolysis to provide a cephalosporin with a —$Ch_2Ch_2$ $R^4$ group at the 3-position where $R^4$ is as defined.

4. In a process for the preparation of a $\Delta^3$-4 -carboxy cephalosporin having at the 3-position a group —$Ch_2CH_2R^4$ wherein $R^4$ is hydrogen, —$CO_2R^5$, -13 $COR^6$, —$CON(R^6)_2$, —$S(O)R^5$, —$S(O)_2R^5$, nitro, lower alkyl, $C_5$ or $C_6$ cycloalkyl, phenyl or cyano; $R^5$ being lower alkyl, benzyl, phenyl, naphthyl, cyclohexyl, or cyclopentyl; $R^6$ being hydrogen or $R^5$; wherein the improvement comprises the step of reacting a $\Delta^2$- or $\Delta^3$-4-carboxy or protected carboxy cephalosporin or the oxide thereof having at the 3-position a group $CH_2$Hal in which Hal is chlorine, bromine or iodine with a phosphorus ylid of the formula:

$$(R^3)_3P=CH—R^4 \qquad (III)$$

wherein the $R^3$ groups, which may be the same or different, are each $C_3$–$C_{10}$ alkyl, $C_5$ or $C_6$ cycloalkyl, phenyl or di(lower alkyl) amino and $R^4$ has the meaning defined above to provide a cephalosporin having at the 3-position a

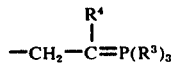

group.

5. In a process for the preparation of a $\Delta^3$-4-carboxy cephalosporin having at the 3-position a group —$CH_2CH_2R^4$ wherein $R^4$ is hydrogen, —$CO_2Rhu$ 5, —$COR^6$, —$CON(R^6)_2$, —$S(O)R^5$, —$S(O)_2R^5$, nitro, lower alkyl, $C_5$ or $C_6$ cycloalkyl phenyl, or cyano; $R^5$ being lower alkyl, benzyl, phenyl, naphthyl, cyclohexyl or cyclopentyl; R6 being hydrogen or $R^5$; wherein the improvement comprises the step of cleaving the carbon-phosphorus bond of a $\Delta^2$- or $\Delta^3$-4-carboxy or protected carboxy cephalosporin or the oxide thereof having at the 3-position a group

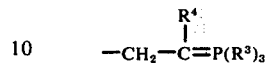

wherein the $R^3$ groups, which may be the same or different, are each $C_3$–$C_{10}$ alkyl,$C_5$ or $C_6$ cycloalkyl, phenyl or di(lower alkyl) amino and $R^4$ has the above defined meaning, by reductively cleaving the carbon to phosphorus bond to provide a —$CH_2CH_2R^4$ group at the 3-position; where $R^4$ is as defined.

6. In a process for the preparation of a $\Delta^3$-4-carboxy cephalosporin having at the 3-position a group —$CH_2CH_2R^4$ wherein $R^4$ is hydrogen, —$CO_2R^5$, —$COR^6$, —$CON(R^6)_2$, —$S(O)_2R^5$, nitro, lower alkyl, $C_5$or $C_6$ cycloalkyl, phenyl, or cyano; $R^5$ being lower alkyl, benzyl, phenyl, naphthyl, cyclohexyl or cyclopentyl; $R^6$ being hydrogen or $R^5$; wherein the improvement comprises the step of cleaving the carbon-phosphorus bond of a $\Delta^2$ or $\Delta^2$-4-carboxy or protected carboxy cephalosporin or the oxide thereof having at the 3-position a group

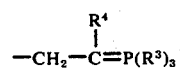

wherein the $R^3$ groups, which may be the same or different, are each $C_3$–$C_{10}$ alkyl, $C_5$ or $C_6$ cycloalkyl, phenyl or di(lower alkyl) amino and $R_4$ has the above defined meaning, by hydrolysis to provide a cephalosporin with a —$CH_2CH_2R^4$ at the 3position where $R^4$ is as defined.

* * * * *